United States Patent [19]
Atkinson

[11] Patent Number: 5,589,898
[45] Date of Patent: Dec. 31, 1996

[54] METHOD AND SYSTEM FOR COLOR VISION DEFICIENCY CORRECTION

[75] Inventor: Holly G. Atkinson, Bridgewater, Conn.

[73] Assignee: Reuters Limited, London, England

[21] Appl. No.: 474,257

[22] Filed: Jun. 7, 1995

[51] Int. Cl.$^6$ ................................ A61B 3/02; A61B 3/00
[52] U.S. Cl. ........................ 351/237; 351/239; 351/242; 351/246
[58] Field of Search .................................... 351/242, 239, 351/246, 240, 241, 243, 222, 238, 237; 358/520; 345/150, 199

[56] References Cited

U.S. PATENT DOCUMENTS

| | | | |
|---|---|---|---|
| 4,634,243 | 1/1987 | Massof et al. ......................... | 351/243 |
| 5,311,212 | 5/1994 | Beretta .................................. | 345/150 |

OTHER PUBLICATIONS

Johannessen et al., *What do Colour–blind People See?*, Nature, Jul. 13, 1995, pp. 127–128.

Nathans, Jeremy, *The Genes for Color Vision*, Scientific American, Feb. 1989.

Foster, David H., *Inherited and Acquired Colour Vision Deficiencies: Fundamental Aspects and Clinical Studies*, Vision and Visual Dysfunction vol. 7, 1991.

Miguel Lugo, M.D. and James S. Tiedeman, M.D., *Computerized Scoring and Graphing of the Farnsworth–Munsell 100–Hue Color Vision Test*, American Journal of Ophthalmology 101:469–.

Edsel B. Ing, M.D. et al., *Computerized colour vision testing*, Can J Ophthalmol, vol 29 No. 3, 1994.

*Primary Examiner*—Hung Dang
*Attorney, Agent, or Firm*—Weil, Gotshal & Manges LLP

[57] ABSTRACT

The present invention is an apparatus and method for the testing of computer users for color vision defects, sometimes referred to as "color blindness," and then the automatic adjustment of color computer displays to settings that are optimal for certain such deficiencies.

11 Claims, 5 Drawing Sheets

METHOD AND SYSTEM FOR COLOR VISION DEFICIENCY CORRECTION

BACKGROUND OF THE INVENTION

Color vision-defects are prevalent in the male population. The majority of congenital color deficiencies affect red-green function. Roughly 8% of Caucasian males have a measurable inability to distinguish between red and green—a deficiency called red-green dichromacy. Often, persons having some degree of color blindness, even a significant degree, are not diagnosed unless they are formally tested or accidentally uncover it through some event. This is particularly the case, since many cases of color vision defects are only mild. Nevertheless, even in these cases, the deficiency can have a noticeable effect on the ability of the person to fully distinguish colors.

Color vision tests are employed clinically to identify and differentiate congenital and acquired color vision deficiencies. These tests are primarily designed to identify people with congenital protan (red) or deutan (green) deficiencies which occur in about 8% of the male population and about 0.5% of the female population. Testing for color vision deficiencies is often done using four principal types of tests: pseudiosochromatic plates, anomaloscopes, arrangement tests (hue discrimination) and lanterns.

Printed pseudiosochromatic plates are the most widely used color vision screening tests. These tests are comprised of a pattern of colored dots, chosen and placed so that a person unable to distinguish red, for example, will be unable to discern a number or a letter formed in red against a setting of other colored dots. If a series of pseudiosochromatic plate tests are presented to the user and the answers correlated after the test is administered, various types of color vision defects can be diagnosed.

Another commonly used type of color vision test is an "arrangement test." Arrangement tests require a person to arrange a number of color chips in order of similarity.

Anomaloscopes have been used for color-vision testing since the late 19th century. These devices work by projecting three different monochromatic lights onto a screen. The anomaloscope relies on the fact that people with normal color vision have two classes of color detectors—the red and the green—operating at the red-to-green end of the color spectrum.

Lantern tests are used to test for color naming and are primarily used to discern signal recognition in maritime, military, aviation and transport services.

In an age when more and more educational, commercial and even entertainment activities take place through use of computers utilizing color monitors, color plays an increasingly important role in conveying information and symbolizing attributes or characteristics. For example, in a computer application, a word or symbol may be presented with green-colored text as a "hot" term—to distinguish it from the rest of the text—connoting a link to other information or some other attribute.

The disadvantages caused by an inability to perceive such a "hot" term are increasingly serious. Computer software, including application programs such as graphics programs, word processing programs and spreadsheet programs, and operating systems and environments such as DOS, OS/2 and Windows, often utilize preset—or default—color palettes on the display which include different colored "hot" terms. While these programs generally permit users to alter the color palette for personal reasons in an ad hoc manner, they are not designed to compensate automatically for any color vision deficiencies of the user. A person with abnormal color vision might or might not succeed in choosing display colors that match his best ability to perceive. The software would give him no active guidance in this respect, merely a passive preview facility.

There is an increasing need, therefore, to provide a structured, reliable deliberate and automatic way of adjusting color displays to correct for color vision defects of computer users. Despite this need, there has never been an apparatus or method for integrating a color vision test with the operation of a computer system to automatically optimize the use of color or other symbols in view of the results of the test. While it is known to use a computer to conduct certain vision tests, such as is reported in Computerized Scoring and Graphing of the Farnsworth-MunseH 100-Hue Color Vision Test, Miguel Lugo and James S. Tiederman, American Journal or Ophthalmology 101:469–474, April, 1986, or Computerized Colour Vision Testing, Edsel B. Ing, John A. Parker and Loft-Anne Emerton, Can. J. Ophthalmol—vol 29, no. 3, 1994, there has not been any recognition of the present invention: using the results of the computerized color vision test to alter the setting of the computer display for the benefit of the user.

SUMMARY OF THE INVENTION

The present invention meets this unfilled need in the prior art. According to the present invention, a computer user is presented on the screen, preferably at the time of startup, with a computerized emulation of a color vision test. Upon completion of the interactive color vision test by the user, the apparatus and method of the present invention analyze the responses entered by the user against a database of information on different varieties of color vision defects and determine the type of any detected color deficiency. The invention then provides appropriate feedback responsive to any defective color vision determined by the test, for example, by suggesting, in one of several manners, what remedial action may be appropriate to optimize, for that user, the screen colors utilized by the various applications.

In a preferred embodiment of the present invention, the apparatus and method may also automatically take affirmative steps to alter the screen colors presented to the user to take account of any perception deficiencies revealed by the test. For example, for a green deficient person, this embodiment of the invention would automatically filter all incoming green text and convert it to another color, either a default color or a color of the individual's choosing. In this way, the person would be able to "see" what he could not see before: that a text word is "hot."

In addition, persons determined by the color vision test to have monochromacy (the inability to distinguish any hues) and to see only different shades of gray would be compensated for by the use of differing lines, fonts, or symbols to create distinguishing elements, in the same way that color would be used.

BRIEF DESCRIPTION OF THE DRAWINGS

These and other objects of the present invention may be understood by referring to the following specification and drawings in which like numerals indicate like components and in which.

DETAILED DESCRIPTION OF THE DRAWINGS

Figure 1:
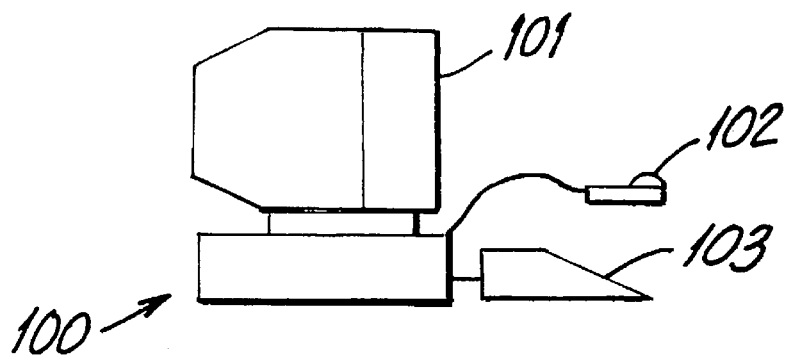
FIG. 1 is a schematic drawing of a computer system according to the present invention.

FIG. 1 shows a computer system including the present invention. As shown, the system includes a computer 100, a display 101, and input means such as a mouse 102 and a keyboard 103. Withing computer 100 are a processor and memory means.

Figure 2:
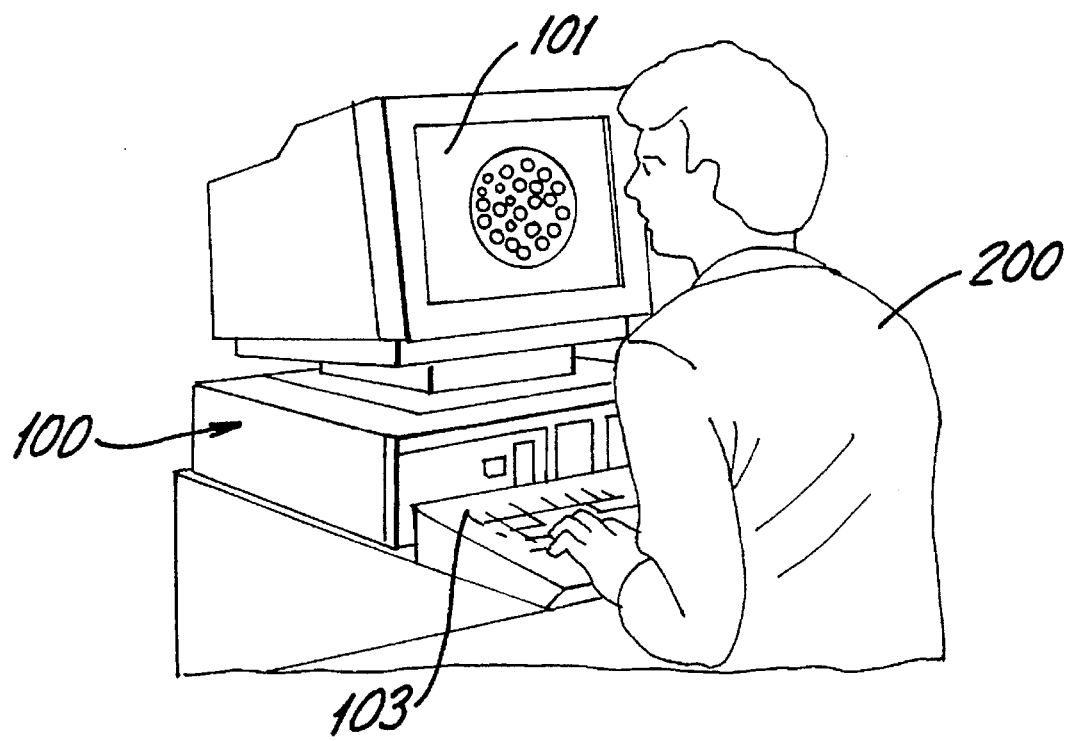
FIG. 2 is an illustrative view of a user using the system and method of the present invention.
Figure 3A:
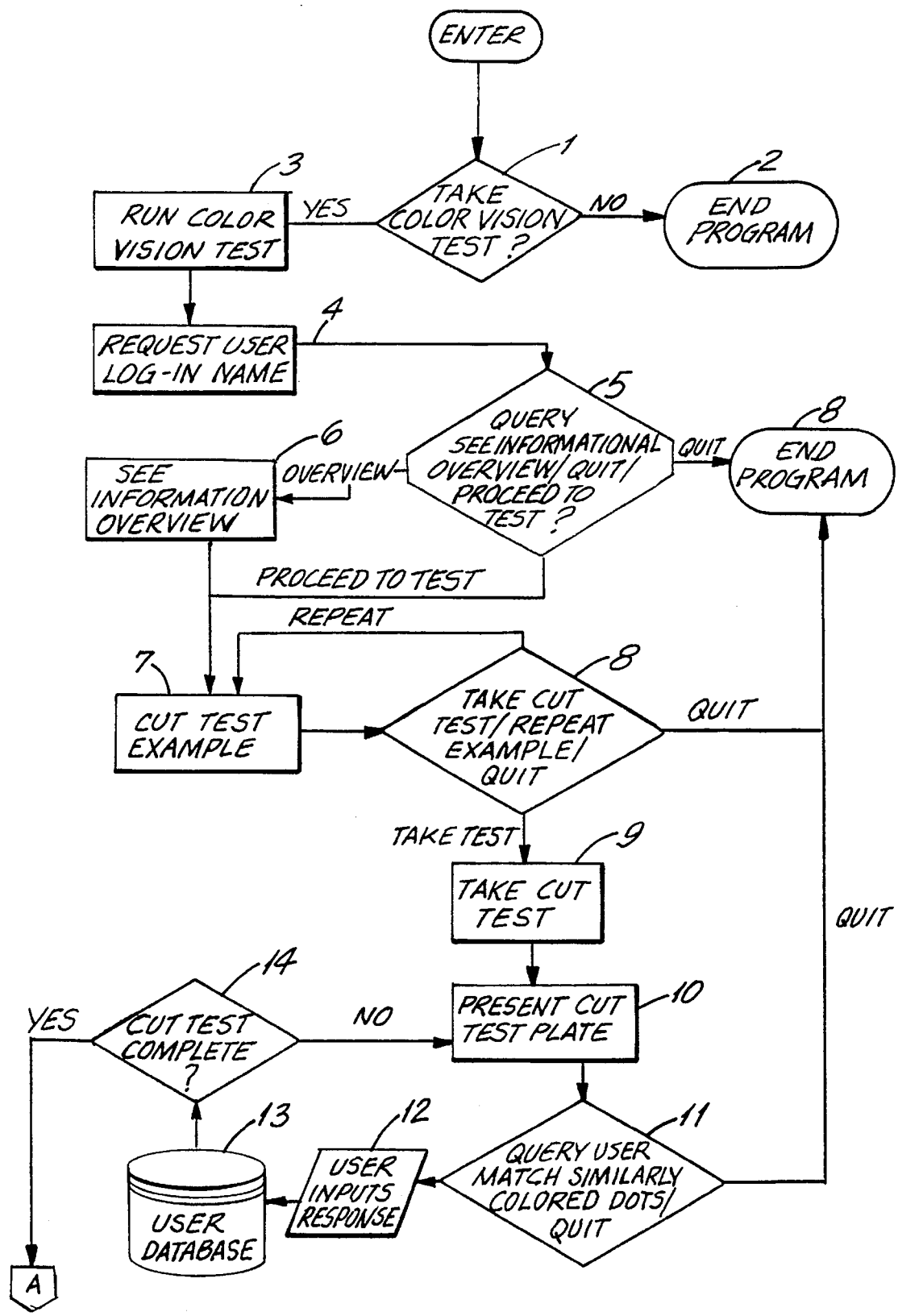
FIGS. 3a, 3b, 3c and 3d together comprise a flow diagram of showing the invention in its method aspect.
Figure 3B:
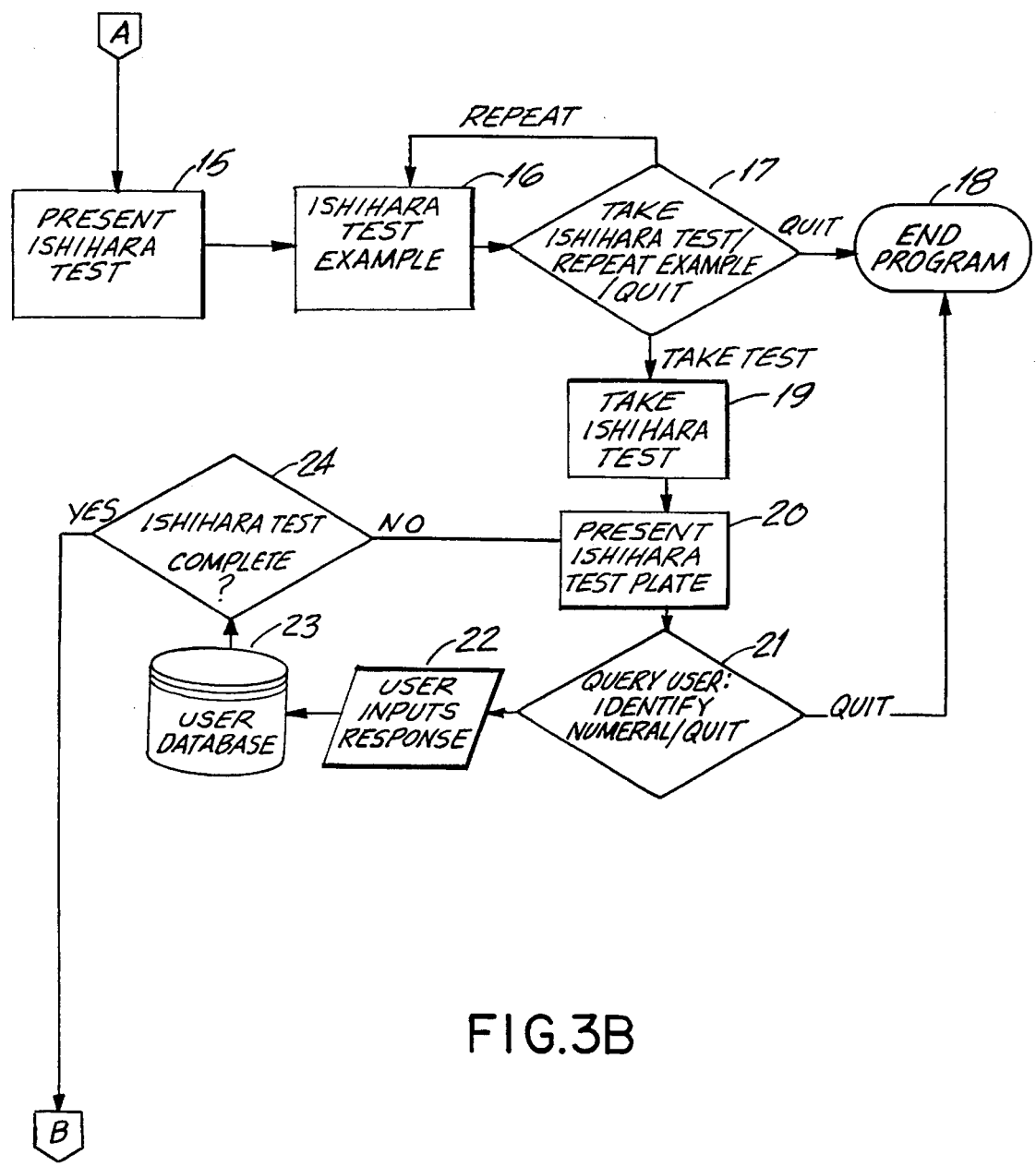
Figure 3C:
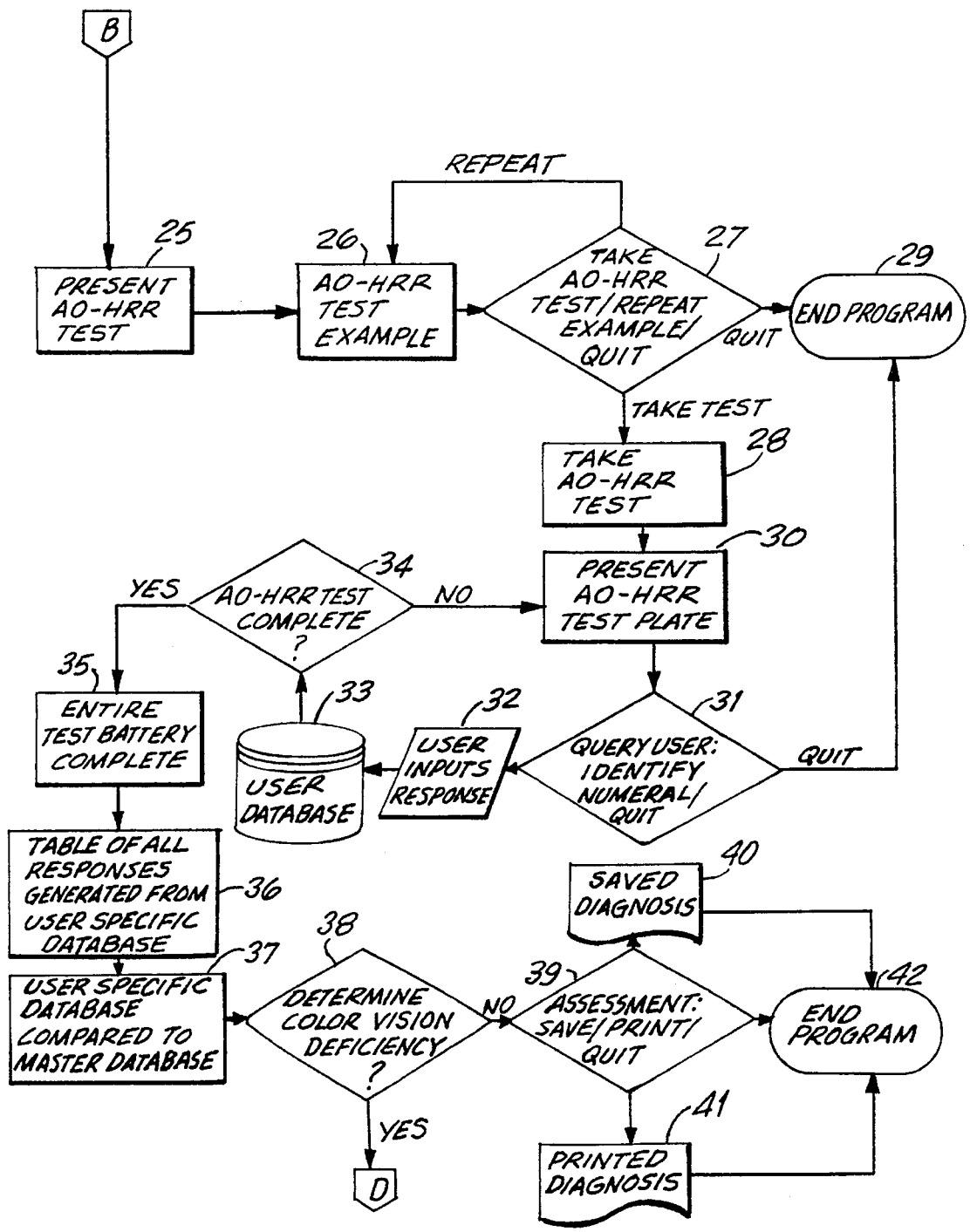
Figure 3D:
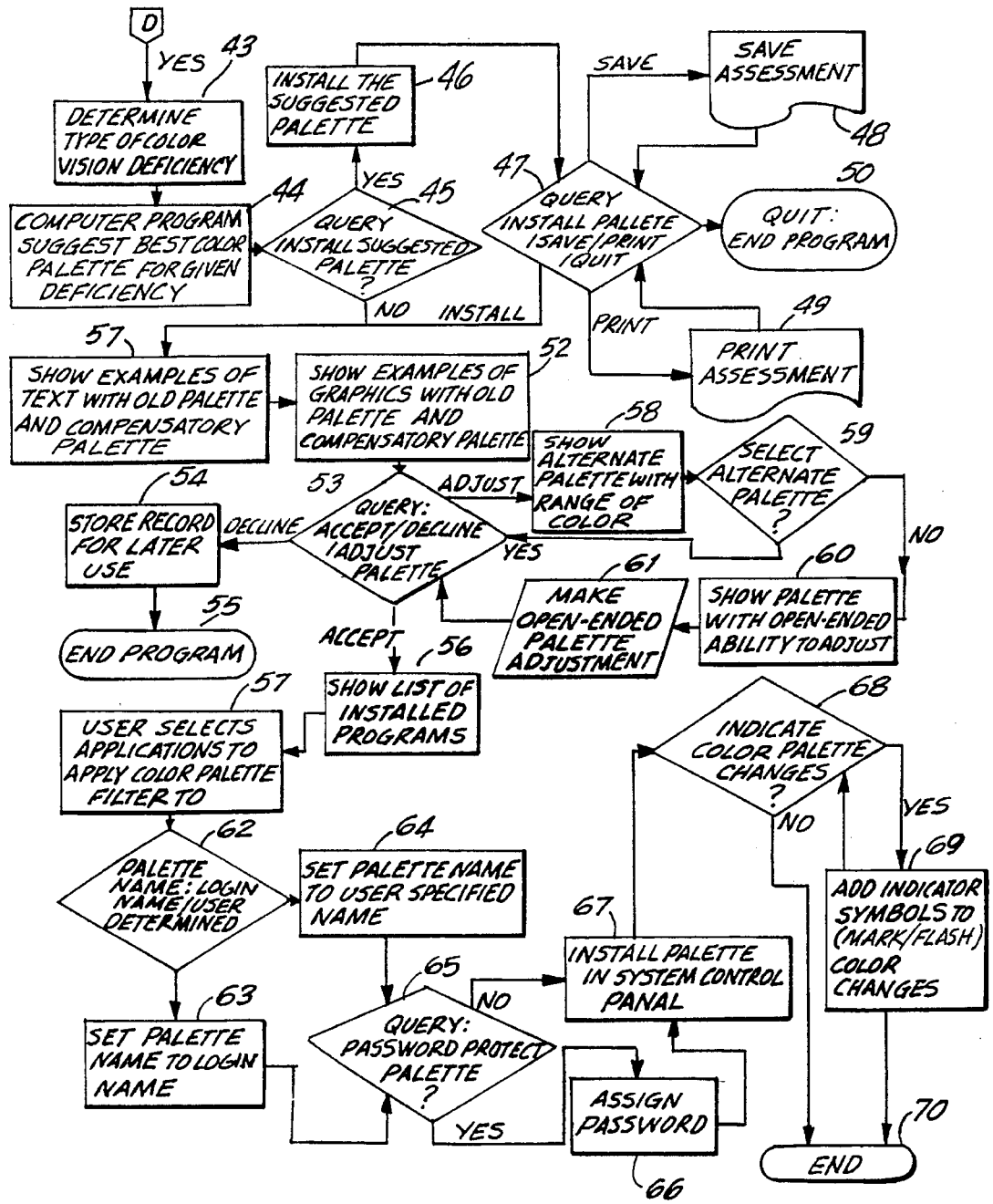

FIG. 2 illustrates a user taking the color vision deficiency test of the present invention. As shown, the user 200 is seated at computer 100 so that he can see the color vision test images displayed on display 101 and enter his responses to questions put to him via keyboard 103.

FIG. 3 shows the invention in its method aspects. In the preferred embodiment shown in this Figure, the invention is utilized by default in the startup routine, but that is not an essential element of the invention. At the user's choice, it could also be invoked manually.

As shown in FIG. 3, when the user turns on the computer, he is presented, as shown in step 1, with a monochromatic text-screen window that asks whether he chooses to take a color vision test which may result in an adjustment of the display colors to compensate for deficiencies that may be determined. The particular message is also not critical to the present invention. Depending on the user's choice, the program branches. Specifically, the user can choose to take the test, not take the test, and, in either case, request that the query not be presented again upon startup. If the user requests that the query not be presented again upon startup, the program will modify necessary resources so as to not initiate itself again upon startup. The user may also choose to terminate the program, as shown in step 2.

It will be understood by those skilled in the art that the various steps discussed here are triggered by the user taking some appropriate action such as clicking on a mouse button or entering a command through the computer keyboard.

As shown in step 3, if the user selects the color vision test, the computer will then run the color vision test/adjustment program. The test is initiated by a request to the user at step 4 to enter a log-in name, so that the color vision/adjustment feature can compensate for multiple users. For example, if two people are using the computer system but only one has a color vision deficiency, the computer will not show a compensatory color palette calibrated for the person determined to have a color vision defect to the person with normal color vision.

Optionally, as shown at step 5, an informational screen may be presented to offer the user the choice of seeing an informational overview, shown in step 6, or of proceeding directly to the test shown in step 7, or of exiting the program as shown in step 8.

The informational overview shown in step 5 will, via stark, high-contrast black and white monochromatic screens which can be seen clearly by all viewers, and, depending on the capabilities of the computer system, via sound, present an informational overview of color vision deficiencies. As mentioned above, the user will have the option of accepting the informational overview and then proceeding to the test, skipping the informational overview and directly taking the test, or exiting the program.

Upon the user's choosing to take the test, the computer program will proceed to present one or more such tests. In the preferred embodiment, a battery of three standard color vision tests is used: the City University Color Vision Test (CUT), the Ishihara test, and the American Optical Hardy-Rand-Rittler test (AO-HRR). For descriptions of these tests, see, e.g., Foster, D. H. Inherited and Acquired Colour Vision Deficiencies, CRC Press, Boca Raton, Fla., 1991; Nathans, J., The Genes for Color Vision, Sci. Am. 1989, Feb.; 260(2):42–9. It should be clearly understood, however, that the particular tests used as not critical to the nature of the present invention.

The initial test, the CUT test, will present a series of test screens comprised of, for example, 4 randomly placed dots with known color assignments, and, again for example, 1 stationery colored dot in the middle. Randomizing the order of the presentation of the dots upon each separate running of the test ensures that the test can never be memorized and therefore will lend itself to higher accuracy.

The user will be shown in step 7 a demonstration of the vision test with the computer playing the part of the user. Following the instruction, at step 8 the user can choose to proceed to take the CUT test, see the example again, or quit. If the user decides to take the test, the computer is programmed to instruct him in steps 12 to pick the dot that most closely resembles the middle dot. The user, using a mouse, keyboard, or other input device, will select the dot that he thinks is closest in color value to the middle dot. The user will preferably, though not necessarily, be permitted only a set amount of (for example, 5 seconds) viewing time per screen. This is preferred merely to keep the test from occupying an inordinate amount of time; extra time taken by the user/subject is not believed likely to affect the test results since a person having a color vision defect cannot remedy that defect by prolonged viewing of the test image. If the user cannot input a response at step 12 within the allocated amount of time, the computer will automatically default to the next screen and enter the data referring to the lack of response into the internal database shown at 13.

The computer, upon receiving a response at step 12, records the response in an internal table 13 within its memory and, at step 14, presents the next plate of the test to the user. The computer will continue presenting test plates and recording responses in this manner for the entire set of CUT test plates.

Upon completion of the battery of plates in the CUT test, the computer proceeds to the Ishihara test at step 15. The user will be shown at step 16 a demonstration of the vision test, with the computer playing the part of the user. Following the instruction the user can choose at step 17 to proceed to take the Ishihara test, see the example again, or quit at step 18. If the user elects to take the Ishihara test, the computer at steps 19 and 20 now presents a series of sets of screens. The first set will present what is called, as will be appreciated by those skilled in art, the "Transformation Design" test, in which a number is seen by persons with normal color vision and a different number is seen by color deficient observers. This section of the test will also be presented in a randomized order generated by the computer, to prevent users from memorizing answers. (The initial plate presented in the Ishihara test is a plate which can be seen correctly by all viewers. This plate is designed to detect malingerers.)

The computer will instruct the user at step 21 to identify the number that he sees on the plate. The user, using a mouse, keyboard, or other input device, will enter the number that he thinks is contained in the plate at step 22, preferably being permitted only a set amount of viewing time (e.g., 5 seconds) per screen. If the user cannot input a response within the allocated amount of time, the computer will automatically default to the next screen and enter the data referring to the lack of response into the internal database 23.

The computer, upon being given a response, tests at step 24 to see if the test has been completed and, if not, presents the next plate of the test, and records the response in an internal table within its memory. The computer will continue presenting test plates and recording responses in this manner for the entire set of the Ishihara Transformation Design test plates.

Upon completion of the battery of plates in the Ishihara Transformation Design test, the computer logs the results in its database 23 and proceeds to the Ishihara "Vanishing Design" test, using the same sequence of steps 19–24 just described with respect to the Transformation Design test. The next set of Ishihara screens will present "Vanishing Designs," in which a number can be seen by persons with normal color vision, but cannot be seen by color deficient people. This section of the test will also be presented in a randomized order generated by the computer to prevent users from memorizing answers. User responses will be recorded into the program's internal table.

Upon completion of the battery of plates in the Ishihara Vanishing Design test, the computer logs the results of the this test and proceeds similarly to perform the "Hidden Digit Design" test and the "Classification Design" test. These tests work in similar fashion to the Transformation Design and Vanishing Design tests, and are similarly presented to the user and scored by the system and method of the present invention. As mentioned, all sections of the test are given in randomized order to prevent users from memorizing answers.

Upon completion of the battery of plates in the Ishihara Classification Design test, the computer logs the results of this test, logs the entire battery of Ishiham test results, and proceeds to the AO-HRR ("American Optical-Hardy, Rand, and Rittler") test at step 25.

The AO-HRR test determines blue deficiency (trim) defects. As before, at step 26 the user will be shown a demonstration of the test with the computer playing the part of the user. Following the instruction the user can choose at step 27 to proceed to take the AO-HRR test at step 28, see the example again, or quit at step 29. If the user proceeds, the computer at step 30 presents a Vanishing Design screen which, as is understood by those skilled in the art, can detect red-deficiency (prom), green deficiency (deutan), blue deficiency (trim), and symmetrical blindness in the same quadrant of each visual field (tetartan).

In a manner similar to that described above for other portions of the test, the user is presented with screen displays embodying the AO-HRR test at step 30, given a limited time to respond at steps 31 and 32, and his responses will be recorded into the program's internal user database table 33. This section of the test will be presented in a randomized order generated by the computer to prevent the memorization of answers.

Upon completion of the AO-HRR test, the user has reached step 35 and completed the entire battery of color vision tests. At this point, the system and method of the present invention generate a table 36 depicting the user's various responses to the full battery of tests. This user-specific table is now compared at step 37 to a database of tables stored within the program. The master database referenced at step 37 contains information relating the test results for the tests provided above to known color vision deficiencies. At step 38 the user is asked whether he wants to proceed to determine the nature of any detected form of color vision deficiency. If he chooses not to proceed in that manner, he is then asked at step 39 whether he wants the assessment generated to that point saved (at step 40), printed (at step 41), or both, and whether he wants at this point to exit the program (at step 42).

If the user, at step 38, elects to continue with the determination of his color vision deficiency, the system proceeds in a manner consistent with the test results. If the user has been determined, by the comparison of his test results as stored in table 36 with the database of known color deficiencies in step 37, to have a color vision deficiency, a description specific to his type of color vision deficiency will be provided visually at step 43. At this point, since no color palette adjustments have been made, this information will be presented, at step 43, via stark, high-contrast black and white monochromatic screens which can be seen clearly by all viewers. The computer will also make an assessment at step 44 as to the most appropriate, optimal computer color display palette that will best compensate for the user's determined color deficiency. At step 45, the user can permit the computer tentatively to install the suggested palette, which will then take place at step 46. The user will also have the option of saving (at step 48), printing (at step 49) or both his color vision diagnosis information, and of exiting the program (at step 50).

It will be noted that the invention at this point provides for a sequence of installation steps. The point of these steps is for the system and method of the present invention to give the user several opportunities to modify the suggested palette as he chooses, rather than to dictate a new palette to him. This is believed to be the preferable way of introducing the compensatory palette to the color deficient user.

Once the suggested compensatory palette has been tentatively installed by the computer at steps 46 and 47, in the preferred embodiment the user is then given another opportunity to confirm the suggested selection. At steps 51 and 52, the computer will alternate showing examples of text and graphics (such as pie charts, and graphical icons/buttons) in various stages (highlighted, grayed out, bold faced, etc.) using first, the previous palette and then the new palette.

The user will be presented with the option to accept, decline or adjust the color palette determined by the computer at step 53. If the user declines the computer-suggested compensatory palette, the computer will retain a record of the user's determined color vision deficiency diagnostics at step 54 and then terminate the program at step 55. Finally, at step 53 the user could choose to further experiment with alternative palettes, despite the program's analysis of the test results. If this option is chosen, the system and method of the present invention at step 58 present one or more alternate palettes to the user, selected in the same manner as described in the above description with respect to the optimal color display palette and give him, at step 59, the ability to choose that alternate palette or, at his option, a user-definable palette. If an alternate palette selected by the system is chosen, the program then returns the user to step 53. If, however, the user decides to define an alternate palette, he is shown his alternatives at step 60 and given the opportunity to choose from among those alternatives at step 60, after which he is returned to step 53.

Once the user has chosen a compensatory palette, the operating system such as OS/2 or the operating environment such as Windows will preferably automatically present, at step 56, a list of all programs installed on the computer and then ask the user at step 57 to select those programs to which to apply his personal color palette. For example, the user would probably want to apply the adjusted color palette to word processing programs or spreadsheets programs, but not to such realistic imaging and processing programs or files such as digital video, photographic picture fries or programs used for graphics painting.

The computer system would then name the chosen compensatory color palette at step 62. The user can either accept his login name for the palette at step 63 or choose a user-specified name at step 64. In either case, the association of a particular compensatory palette with a particular user permits the system to be multiuser but still, at the same time, to have individual compensatory palettes. With this arrangement in effect, each user's custom compensatory palette would not dominate the system, and another palette can be automatically called into use when another user signs onto the system. For example, the user, logged in as "Bob Smith" would be asked by the program if the color palette should be saved in the operating system's Colors control panel under the name "Bob Smith" or under the type of color deficiency he has, e.g. "Protan Color Palette" or "Bob Smith/Protan Color Palette," or a name of the user's own choosing. Said palette would coexist with the different color schemes such as "Ocean" and "Arizona." This palette could also be password-protected, as shown at steps 65 and 66 (where the password is chosen), so that only the user could authorize its deletion or modification. This would alleviate fears of deletion by casual use or intentional mischief.

As is apparent from the discussion contained in the two preceding paragraphs, in the preferred embodiment of the present invention, the testing of the user and the provision of one or more compensatory palettes suggested according to the present invention is integrated with one or more of the popular personal computer operating systems or environments such as Windows, OS/2, and Macintosh OS, where it is interchangeable with other default palettes contained within those operating systems or environments. In the case of Windows, for example, the palette could be located in the Control Panel at step 67 and the user then given, at step 68, the option of selecting it from among the other palettes offered by the Control Panel.

Once this palette is chosen, the computer will install and initiate said palette into the system of the user's machine. The program will now exit at step 70.

Step 69 indicates, as another feature of the present invention, that, at the user's option, the portions of a displayed or printed document having one or more colors altered as a result of the color vision deficiency assessment of the present invention can be indicated by the use of some character or by causing those portions to blink or pulsate on the display.

The underlying computer system technology that will operate the invention will be apparent to those skilled in the art. At its most basic level, it will consist of the following. By means of a low-level markup language, all internal references to text or object-oriented graphics are tracked at all times by the computer system. When a specific color is recognized by the computer, when operating according to the present invention (as determined from the user's color deficiency test), the program will branch to a subroutine or the like which will cause a replacement or substitution of the preset color value by a color value more appropriate for the particular user, as determined from the results of the tests taken by the user at an earlier time as described above.

Moreover, in the preferred embodiment of the present invention, the substitute or replacement color values will depend on the particular use of the color in the particular application. For example, if color x is the background to a bar graph, the program will change it to color y. However, if color x is the foreground color of a word processing document, it will change it instead to color z. Colors y and z, it will have been previously determined, are of differing appropriateness in the two applications.

Similarly, the program will also monitor what program is in use by the user and will, as set when the user specified in step 57, toggle whether or not to apply color value changes as needed.

An important addition to the program's functionality can be utilized when printing color charts and graphs, etc., to either Postscript or HPPL printers. At the user's option, for example, through an entry in the Print Dialog box, the program can also filter colors as they are being printed and substitute a color value for another. In this way, the chart can print in normal colors if intended for general audiences, or in substitute colors to account for the user's own color vision deficiencies.

In a preferred embodiment, as indicated, the color vision test/adjustment feature may be located within the Main Control Panel of Windows, in the color program, where an access method such as a mouse button or keyboard command can call up the test/adjustment feature.

Other modifications and enhancements will occur to persons skilled in the art that do not depart from the spirit and scope of the present invention.

I claim:

1. A method for determining color vision defects of a user of a computer system comprising a processing means, display means, input means and memory means, and for altering a color palette displayed on the display means to compensate for any color vision defect comprising the steps of:

a. storing in the memory means data comprising a plurality of color vision test images and medical information on color vision deficiencies;

b. causing the processing means sequentially to place one or more of the test images on the display means;

c. providing the user with certain instructions concerning his perception of the content of each displayed image;

d. receiving the user's response to the instruction as entered through the input means, e. storing the response in the memory means;

f. comparing in the processing means the user's response with medical information on color vision deficiencies stored in the memory means to determine the nature of the user's color vision deficiency;

g. storing in the memory means a plurality of color palettes for the display means, at least one of which palettes compensates for color vision deficiencies;

h. determining, in response to the comparing step, which of the plurality of color palettes is optimal in view of the user's color deficiency as determined from his responses; and i. causing the system to set the display means to display the optimal color palette.

2. The method of claim 1 wherein the question causing the user to test his color vision appears on the display screen with the color test image.

3. The method of claim 1 wherein the images are displayed in a random sequence.

4. The method of claim 1 wherein the computer system further includes a printer and further including the step of permitting the user to save in the memory means or print on the printer information from the memory means relating to any color vision deficiency determined by the method.

5. The method of claim 1 wherein the system further includes a printer and further including the step of permitting the user, during the process of printing material generated by an application, to decide whether to print the material in the normal colors or in colors corresponding to the optimal color palette.

6. In a computer system consisting of a processing means, display means, input means and memory means, a method for adjusting the color settings of the display means for the convenience of a user having a color vision deficiency, comprising the steps of:

a. storing in the memory means data comprising a plurality of color vision tests associated images and the information concerning the actual content of the test images;

b. causing the processing means to place a test image from one of the color vision tests on the display means;

c. providing to the user (i) information from the memory means concerning the actual content of the displayed test image, (ii) means for selectively altering the hue of the one of the colors being tested in the displayed test image;

d. receiving the user's response in the form of an alteration in the hue selected by the user and entered through the input means;

e. storing the selected alterations in the memory means; and f. causing the processing means to repeat steps a. through e. until all the images have been displayed.

7. The method of claim 6 wherein the means for selectively altering the hue of one of the colors being tested for are a mouse or a keyboard.

8. A computer system for determining color vision defects of a user comprising:

a. memory means containing:

(1) data comprising a plurality of color vision test images and associated instructions questioning the user concerning his perception of the content of each image, (2) medical information relating users perceptions to the test images to known color vision deficiencies, (3) the user's responses to the test images and instructions, and (4) a plurality of color palettes for the display means, at least one of which palettes compensates for color vision deficiencies;

b. display means;

c. processing means;

d. means for sequentially placing on the display means one or more of the test images and the associated instructions;

e. input means for receiving the user's responses to the instructions associated with each image;

f. means for storing the user's responses in the memory means;

g. means for comparing in the processing means the user's responses with the medical information to determine the nature of the user's color vision deficiency;

h. means for determining, in response to the comparing step, which of the plurality of color palettes stored in the memory means is optimal in view of the user's color deficiency; and i. means for setting the display means to display the optimal color palette.

9. The system of claim 8 wherein the display means displays the images in a random sequence.

10. The system of claim 8 further including:

j. a printer; and k. means for permitting the user to save in the memory means or print on the printer information from the memory means relating to any determined color vision deficiency.

11. The system of claim 8 further including:

j. a printer; and k. means for permitting the user, during the process of printing material generated by an application program operating on the system, to decide whether to print the material in the normal colors or in colors corresponding to the optimal color palette.

* * * * *

UNITED STATES PATENT AND TRADEMARK OFFICE
CERTIFICATE OF CORRECTION

PATENT NO. : 5,589,898
DATED : December 31, 1996
INVENTOR(S) : Holly G. Atkinson It is certified that error appears in the above-indentified patent and that said Letters Patent is hereby corrected as shown below:

Column 2, Line 16   delete "MunseH", add --Munsell--

Column 2, Line 20   delete "Loft-Anne", add --Lori-Anne--

Column 5, Line 36   delet "Ishiham", add --Ishihara--

Column 5, Line 39   delete  "(trim)", add --(tritan)--

Column 5, Line 48   delete  "(prom)", add --(protan)--

Column 5, Line 49   delete  "(trim)", add --(tritan)--

Column 7, Line 6    delete  "fries", add --files--

Signed and Sealed this

Twenty-fifth Day of March, 1997

Attest:

BRUCE LEHMAN

*Attesting Officer*    Commissioner of Patents and Trademarks